United States Patent
Deichmann et al.

(10) Patent No.: US 10,299,865 B2
(45) Date of Patent: *May 28, 2019

(54) 3D SYSTEM AND METHOD FOR GUIDING OBJECTS

(71) Applicant: 3Shape A/S, Copenhagen K (DK)

(72) Inventors: Nikolaj Deichmann, Klagshamn (SE); Rune Fisker, Virum (DK)

(73) Assignee: 3SHAPE A/S, Kobenhavn K (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/685,417

(22) Filed: Aug. 24, 2017

(65) Prior Publication Data

US 2017/0367770 A1    Dec. 28, 2017

Related U.S. Application Data

(63) Continuation of application No. 15/089,855, filed on Apr. 4, 2016, now Pat. No. 9,763,746, which is a
(Continued)

(51) Int. Cl.
*H04N 7/18* (2006.01)
*A61B 34/20* (2016.01)
(Continued)

(52) U.S. Cl.
CPC ............ *A61B 34/20* (2016.02); *A61B 5/0062* (2013.01); *A61B 5/0088* (2013.01); *A61B 5/489* (2013.01);
(Continued)

(58) Field of Classification Search
CPC ..... A61B 34/20; A61B 17/176; A61B 5/4893; A61B 5/0062; A61B 5/489; A61B 5/0088;
(Continued)

(56) References Cited

U.S. PATENT DOCUMENTS

| 5,562,448 A | 10/1996 | Mushabac |
|---|---|---|
| 6,527,708 B1 | 3/2003 | Nakamura |

(Continued)

FOREIGN PATENT DOCUMENTS

| DE | 10259250 A1 | 7/2004 |
|---|---|---|
| EP | 1177773 A1 | 2/2002 |

(Continued)

OTHER PUBLICATIONS

First Office Action issued in corresponding Chinese Patent Application No. 2018041301647310, dated Apr. 18, 2018, with English Translation only (8 pages).
(Continued)

*Primary Examiner* — Robert Chevalier
(74) *Attorney, Agent, or Firm* — Buchanan Ingersoll & Rooney PC

(57) ABSTRACT

A method for providing a guided relative movement of a first object and a second object includes obtaining the first object; obtaining the second object and a 3D model of the second object, and deriving from the 3D model a first preferred relative arrangement between the first and second objects; obtaining a pre-process plan describing a preferred path for the relative movement of the first and second objects towards the first preferred relative arrangement; performing a movement procedure that includes 3D scanning at least a region of said second object using the 3D scanner and determining a present relative arrangement of the first and second objects from a result of the 3D scanning; calculating information for correcting in real-time for deviation in the relative movement from the preferred path; and providing a relative movement of the first and second objects towards the first preferred relative arrangement.

19 Claims, 9 Drawing Sheets

Related U.S. Application Data continuation of application No. 14/110,184, filed as application No. PCT/DK2012/050112 on Apr. 4, 2012, now Pat. No. 9,320,572.

(60) Provisional application No. 61/472,858, filed on Apr. 7, 2011.

(51) Int. Cl.
| | |
|---|---|
| *A61B 17/17* | (2006.01) |
| *A61C 1/08* | (2006.01) |
| *A61B 5/00* | (2006.01) |
| *A61C 3/02* | (2006.01) |
| *A61C 8/00* | (2006.01) |

(52) U.S. Cl.
CPC .......... *A61B 5/4893* (2013.01); *A61B 17/176* (2013.01); *A61C 1/082* (2013.01); *A61C 1/084* (2013.01); *A61C 3/02* (2013.01); *A61C 8/0089* (2013.01); *A61B 2034/2055* (2016.02); *A61B 2034/2065* (2016.02)

(58) Field of Classification Search
CPC .... A61B 2034/2065; A61B 2034/2055; A61C 8/0089; A61C 3/02; A61C 1/084; A61C 1/082
USPC .......... 348/66, 42, 65, 64, 45; 386/200, 210, 386/223, 224
See application file for complete search history.

(56) References Cited

U.S. PATENT DOCUMENTS

| | | | |
|---|---|---|---|
| 9,320,572 | B2 | 4/2016 | Deichmann et al. |
| 2001/0027272 | A1 | 10/2001 | Saito et al. |
| 2005/0015099 | A1 | 1/2005 | Momoi et al. |
| 2006/0189842 | A1 | 8/2006 | Hoeg et al. |
| 2007/0018975 | A1 | 1/2007 | Chuanggui |
| 2007/0238981 | A1 | 10/2007 | Zhu et al. |
| 2009/0093715 | A1 | 4/2009 | Downey et al. |
| 2009/0177081 | A1 | 7/2009 | Joskowicz et al. |
| 2009/0216114 | A1 | 8/2009 | Gorges et al. |
| 2009/0316966 | A1* | 12/2009 | Marshall .............. A61B 6/5217 382/128 |
| 2011/0273757 | A1 | 11/2011 | Kobayashi |

FOREIGN PATENT DOCUMENTS

| | | |
|---|---|---|
| EP | 1 498 081 A1 | 1/2005 |
| JP | 2000-279425 A | 10/2000 |
| JP | 2005-030911 A | 2/2005 |
| WO | WO 2006/075331 A2 | 7/2006 |
| WO | WO 2006/089426 A1 | 8/2006 |
| WO | WO 2010/096634 A1 | 8/2010 |

OTHER PUBLICATIONS

International Search Report (PCT/ISA/210) dated Jun. 29, 2012, by the Denmark Patent Office as the International Searching Authority for International Application No. PCT/DK2012/050112.

English language translation of First Office Action dated Mar. 20, 2015, by the Chinese Patent Office in corresponding Chinese Patent Application No. 201280025644.5. (22 pages).

European Search Report issued in corresponding European Patent Application No. 12768342.3, dated Nov. 3, 2014 (6 pages).

An English Translation of Office Action (Notice of Reasons for Rejection), dated Feb. 16, 2016 by the Japanese Patent Office in corresponding Japanese Patent Application No. 2014-502996. (4 pages).

* cited by examiner

3D SYSTEM AND METHOD FOR GUIDING OBJECTS

The present application is a continuation of U.S. application Ser. No. 15/089,855, which was filed on Apr. 4, 2016, which is a continuation of application Ser. No. 14/110,184, which was filed in the US on Dec. 5, 2013, and which is a national stage application of PCT/DK2012/050112, filed on Apr. 4, 2012, and which claims the priority of U.S. Provisional Application No. 61/472,858, filed on Apr. 7, 2011, and Danish patent application number PA 2011 00270, filed on Apr. 7, 2011. The contents of U.S. application Ser. No. 15/089,855; PCT/DK2012/050112; U.S. Provisional Application No. 61/472,858; and Danish patent application number PA 2011 00270 are all incorporated herein by reference.

The disclosure relates to a method and a 3D guiding system for providing a guided relative movement of a first and a second object. More particularly, the disclosure relates to a method and a 3D guiding system configured for calculating information for guiding the relative movement of the first and second objects towards a first preferred relative arrangement, which may be determined from a 3D model of the second object. The present relative position of the two objects is tracked by 3D scanning of the second object.

Disclosed is a 3D guiding system for guiding a relative movement of a first object and a second object, where the system is configured for being arranged in relation to said first object, and where said 3D guiding system comprises:
- a 3D scanner configured for performing a 3D scanning of the second object;
  - a non-transitory computer-readable medium configured for at least temporary storing:
    - a 3D model of the second object;
    - program code for determining a present relative arrangement of the first and second objects from a result of a 3D scanning of the second object; and
    - program code for calculating information for guiding the relative movement of the first and second objects towards a first preferred relative arrangement from said present relative arrangement.

Disclosed is a method for providing a guided relative movement of a first object and a second object, said method comprising:
- obtaining the first object onto which a 3D guiding system is attached, where said 3D guiding system comprises a 3D scanner;
- obtaining the second object and a 3D model of the second object, and deriving from said 3D model a first preferred relative arrangement between the first and second objects;
- performing a movement procedure comprising:
  - a) 3D scanning at least a region of said second object using said 3D scanner and determining a present relative arrangement of the first and second objects from a result of the 3D scanning;
  - b) calculating information for guiding the relative movement of the first and second objects towards said first preferred relative arrangement from said present relative arrangement; and
  - c) providing a relative movement of said first and second objects towards the first preferred relative arrangement, where the calculated information is used for guiding the relative movement.

In some embodiments, the non-transitory computer-readable medium further stores program code for deriving from said 3D model a first preferred relative arrangement between the first and second objects. Deriving the first preferred relative arrangement may involve resource demanding calculations and in some embodiments, it may be preferred that first preferred relative arrangement is derived on a separate system from which it then transferred to the 3D guiding system.

In some embodiments, the second object is part of the system. In some embodiments, the second object and the first object are autonomous parts.

In some embodiments, the system and/or the 3D guiding system comprises a device configured to provide a relative movement of said first and second objects towards the first preferred relative arrangement, where the calculated information is used for guiding the relative movement.

In some embodiments, the 3D guiding system comprises a signal light source configured to provide said information by projecting a guiding signal onto a target region of the second object.

In some embodiments, the system and/or the 3D guiding system comprises a non-transitory computer readable medium having one or more computer instructions stored thereon, where said computer instructions comprises instructions for performing the method according to the disclosure.

An advantage of the present disclosure over the prior art is that the present relative arrangement of the first and second objects is determined without using an external localization device.

In some embodiments, determining the present relative arrangement of the first and second objects comprises pairing the obtained 3D model of the second object and the result of the 3D scanning, such that the result of the 3D scanning is compared to the obtained 3D model and from the comparison the present relative arrangement of the first and second objects is determined.

The comparison may comprise a rotation and a translation of the obtained 3D model and the result of the 3D scanning such that they are aligned correctly, e.g. with corresponding surfaces coinciding. Based on the extent of rotation and translation required to provide a correct alignment, the present relative arrangement can be determined with respect to the first preferred relative arrangement.

The result of the 3D scanning may be used to generate a new 3D model mapping the surface and/or the interior structure of the second object in the scanned region. Pairing the new 3D model and the obtained 3D model may then be used to determine the present relative orientation of the first and second objects with respect to the first preferred relative arrangement.

In some embodiments, the obtained 3D model relates to a surface of the second object, such that the 3D model comprises data relating to a surface of a scanned region of said second object. This may for example be the case when the 3D scanner is an optical scanner and the scanned region of the second object is such that light is reflected from its surface. It may also be the case when the 3D scanner is based on focus scanning, such as in the 3Shape TRIOS intraoral scanner, and the surface of the second object is at least partly translucent, which e.g. can be the case for teeth.

Further characteristics of the second object may be added to the 3D model obtained by scanning the surface of the second object. These characteristics may comprise an interior structure in the second object. This may be the case when the second object is a dental situation or a body part of a patient where the further characteristics may be obtained e.g. by X-ray imaging of the second object. The further characteristics may be integrated in the 3D model of the second object.

In some embodiments obtaining said 3D model comprises a sub-surface scanning of the scanned region and/or the target region of said second object, such as by Magnetic Resonance Imaging, by an X-ray scanning or by a CT scanning of the second object, such that the 3D model comprises data relating to an interior structure of said second object.

In some embodiments, the 3D scanner of the guiding system is configured for sub-surface scanning. The 3D scanner may e.g. be a CT scanner where the surface in the scanned region of the second object is at least partly transparent to the X-ray signals of the CT scanner. The movement procedure can then be guided based on the knowledge of the interior structure and on the measurements provided by the CT scanner. Likewise, the first preferred relative arrangement and the information can then be derived from the interior structure, such that a guiding signal displayed e.g. on the surface of the second object is derived from the interior structure.

In some embodiments, the obtained 3D model comprises both a surface and an interior structure of the second object.

In a dental application of the disclosure, the obtained 3D model may comprise both the surface and interior structure of a set of teeth. If a new 3D model is generated from the result of the 3D scanning, the set of teeth in the new 3D model may virtually be rotated and/or translated to coincide with the set of teeth in the obtained model.

In a surgical application of the disclosure, the obtained 3D model may comprise both the surface, such as the skin surface, and an interior structure of a body part, such as veins, arteries and bones.

In some embodiments, the shape of first object is taken into account when deriving the first preferred relative arrangement between the first and second objects.

This may be the case e.g. when a cross sectional shape of the first object at a point of contact with the second object has no rotation symmetry or a finite rotational symmetry, such as a two-fold or a three-fold symmetry.

The reduced rotation symmetry may be around a longitudinal axis of the first object. When the first object comprises a surgical scalpel, there may be no rotation symmetry since the surgical scalpel has a preferred orientation relative to the surface with the sharp edge facing the surface which it is intended to cut into.

A dental drill also has a shape with a preferred relative arrangement relative to a tooth from which toot material is to be removed by the drill or relative to the mandibular/maxillary from which bone material is to be removed in order to make space for an implant.

In some embodiments, the 3D guiding system comprises several parts.

In some embodiments, the 3D guiding system may be an integrated system with all parts integrated in one coherent system.

In some embodiments, the 3D guiding system comprises two or more separate parts that are distributed with a distance between at least some of said parts. For a 3D guiding system comprising separate parts, all of these separate parts may be attached to the first object. The attachment may be direct or indirect, such as an attachment via another of the separate parts.

In some embodiments, the distance between the first and second objects is determined from the result of the 3D scanning. The scanning may e.g. comprise a time of flight based measurement of the distance and/or a scaled version of the 3D model is fitted to the result of the 3D scanning. A scaling factor showing the size of the scaled version of the 3D model at different distances can be used to determine the distance.

In some embodiments, the first preferred relative arrangement is such that the first object is adjacent to the second object with a preferred orientation relative to the second object. This may be the case for a number of applications of the disclosure, such as in dental treatments, in surgical operations, in the gluing together two objects, in parking a car relative to another car or an obstacle, or in docking one object in relation to another.

In the context of the present disclosure, the phrase "adjacent" may refer to an arrangement where one object is next to but not necessarily connected with a another object. The object can also be in contact, such as in contact with no penetration of one object into the other.

In some embodiments, the first preferred relative arrangement is such that there is a well-defined and/or predetermined distance between the first object and the second object with a preferred relative orientation of the two objects. This may e.g. be the case when the disclosure is applied in relation to a welding procedure or a parking of a vehicle.

In the context of the present disclosure the phrase "X determined from Y" may refer to the case wherein determining X takes into account Y. Other parameters may still influence the value of X. X may for instance be the present relative arrangement while Y may be a result of the 3D scanning.

In the context of the present disclosure the phrase "towards the first preferred relative arrangement" may refer to a relative movement which brings the first and second object closer to the first preferred relative arrangement, such as a relative movement which brings the first and second object to the first preferred relative arrangement.

During the relative motion of the first and second objects, the second object may be stationary relative to a reference frame, while the first object is moved towards the second object. The method may then be for providing a guided movement of the first object.

This may be the case when the disclosure is used in relation to a dental or a surgical procedure on a patient. In relation to dental treatments the disclosure may be used to guide e.g. a dental drilling tool used to drill into a tooth or the mandibular or maxillary bone of the patient. In relation to surgical treatments the disclosure may be used to guide e.g. a surgical scalpel used to provide a cut in the patient.

During the relative movement of the first and second objects, the first object may be stationary relative to a reference frame, while the second object is moved towards the first object. The method may then be for providing a guided movement of the second object.

Such a configuration may e.g. be used when the first object is the heavier of the first and second objects.

The relative movement of the first and second objects may comprise a movement of both the first object and the second object relative to a reference frame. This may e.g. be the case when both the first object and the second object can be moved in a controlled manner.

The movement procedure may involve one or more steps that are performed in real-time. One or more of a), b) and c) may be performed in real-time.

The 3D scanning of the scanned region of the second object may be performed in real-time. The calculation of the information may be performed in real-time.

In some embodiments, the 3D guiding system is configured for 3D scanning of the scanned region of the second object and/or for calculation of the information and/or for displaying said information in real-time.

The information may be displayed in real—both when a human operator and a robotic device or another machine provides the relative motion of the first and second objects.

In some embodiments, the 3D guiding system is configured for executing the program code for determining the present relative arrangement and/or for executing the program code for calculating information in real-time.

In the context of the present disclosure, the phrase "real-time" refers to the situation where the function that is performed in real-time is sufficiently rapid such that e.g. a guiding signal is provided sufficiently rapid such that an operator can adjust the relative movement of the first and second objects in due time.

For dental and/or surgical applications of the disclosure, the phrase "real-time" may be used for situations where the function occurs within a time frame of seconds, such that the information can be calculated and provided to the dentist or doctor in a manner such that the information is provided with a rate that is faster than the movement of the dental drilling tool or the scalpel.

Real-time may mean in that the function occurs within a time interval, where said time interval is less than about 60 seconds, such as less than about 30 seconds, such as less than about 15 seconds, such as less than about 10 seconds, such as less than about 5 seconds, such as less than about 2 seconds, such as less than about 1 second, such as less than about 0.5 seconds, such as less than about 0.2 seconds, such as less than about 0.1 seconds, such as less than about 0.05 seconds, such as less than about 0.02 seconds, such as less than about 0.01 seconds, such as less than about 0.005 seconds, such as less than about 0.002 seconds, such as less than about 0.001 seconds.

In some embodiments, the relative movement is controlled by a human operator. The first object and/or the second object may be a handheld device which the operator can move relative to the other object. The operator may also control the relative movement via a mechanical device configured for translating, moving, tilting or rotating an object, such a mechanical arm, an engine, or a stage.

In some embodiments, the relative movement is computer controlled. This may e.g. be the case for a robotic device according to the present disclosure, where the 3D guiding system and/or method assist the robotic device in the relative motion of the first and second objects.

In some embodiments, the movement procedure comprises repeating one or more of a), b) and c) a number of times, such that the first and second objects may gradually approach the first preferred relative arrangement.

The repetition of a), b) and c) may be such that both a) and b) are performed for each repetition of c). The present relative arrangement of the first and second objects is then determined and the information for guiding the relative motion is then calculated for each relative movement of the objects.

The repetition of a), b) and c) may be such that either a) or b) is performed for one repetition of c). This may be the case when the present relative arrangement of the first and second objects is determined for each relative movement of the objects, while the calculation of the information for guiding the relative motion only is calculated when a significant change of the relative arrangement has occurred.

In some embodiments, the relative movement of the first and second objects is substantially continuous and a) and/or b) are performed during the relative movement. For several applications of the disclosure, the relative motion of the first and second objects is substantially continuous such as when a human operator or a robotic device moves one object towards another in a smooth movement while using the calculated information for guiding the motion.

The determining of the present relative arrangement and the calculation of the information may be performed on the fly. Both a) and b) should then preferably be sufficiently fast compared with the speed of the movement, such that the information is provided in due time for appropriate changes in e.g. the direction of the relative movement to be made. In some embodiments, b) is only performed if a) indicates that a significant change in the relative arrangement has occurred since the previous calculation of the information.

In some embodiments, the 3D guiding system is configured for continuously executing the program code for determining the present relative arrangement and/or for continuously executing the program code for calculating information and/or for executing the program code for deriving further preferred relative arrangements, such that these program codes can be executed continuously during a relative movement of the first and second objects.

In some embodiments, the method comprises arranging said first and second objects in an initial relative arrangement and where said information is used for guiding the first and second objects from the initial relative arrangement to the first preferred relative arrangement.

In some embodiments, the calculation of the information also provides or is based on a calculated planned movement, such as a planned movement based on a previous relative arrangement and the first preferred relative arrangement of the first and second objects. The previous relative arrangement may be the initial relative arrangement or a relative arrangement occurring between the initial and the current relative arrangement.

Not all steps needs to be performed in real-time. For instance the calculation of information may occur with a lower repetition rate than e.g. the 3D scanning. When the 3D scanning shows that the relative movement of the first and second objects occurs as planned, there is no need for providing information to the operator after the acquiring of each 3D scan.

In some embodiments, the 3D guiding system comprises a motion sensor adapted to perform a motion measurement of the movement of the first object When the 3D guiding system comprises a motion sensor the present relative arrangement of the first and second objects can determined from said motion measurement. The present relative arrangement can be determined from the motion measurement alone or in combination with information derived from a 3D scanning of the second object and the 3D model.

In some embodiments, the program code for determining said present relative arrangement takes into account a result of the motion measurement, such that the present relative arrangement of the first and second objects can be determined from said motion measurement.

In some embodiments, the 3D guiding system comprises an orientation sensor adapted to perform an orientation measurement of the first object.

When the 3D guiding system comprises an orientation sensor the present relative arrangement of the first and second objects is determined from said orientation measurement. The present relative arrangement can be determined from the orientation measurement alone or in combination with information derived from a 3D scanning of the second object and the 3D model.

In some embodiments, the program code for determining the present relative arrangement takes into account a result of the orientation measurement, such that the present relative arrangement of the first and second objects can be determined from said orientation measurement.

The present relative arrangement can be determined from the orientation measurement and the motion measurement in combination.

From a well-defined initial relative arrangement the motion sensor and/or the orientation sensors may be used to determine the present relative arrangement at various positions on the way to the first preferred relative arrangement.

In some embodiments, the 3D scanning is performed using said 3D scanner.

In some embodiments, the first object contacts said second object in a target region of the second object when the first and second objects are arranged in said first preferred relative arrangement. The target region may comprise the point of contact between the first and second objects and optionally the immediately surrounding surface of the second object.

In some embodiments, the first object comprises a distal end which is configured to contact the target region of the second object. The distal end may comprise an entry part configured to enter the target region of said second object. The shape of the entry part of said first object may be taken into account when the first preferred relative arrangement is derived.

In some embodiments, the first object comprises a proximal end which is configured for being held by an operator or by a mechanical device such as a robot.

In some embodiments, the information is displayed using an information displaying device of said 3D guiding system, where the information displaying device is configured for displaying the information to an operator.

The information displaying device may be an integral part of the 3D guiding system which is arranged at the first object. In the case where the first object is a "handheld" device, the information displaying device can be part of what is handheld.

The information displaying device can in principle also be arranged at some distance from the first object, such as e.g. when the information displaying device is a device connected to the handheld first object via a wired or a wireless connection.

In some embodiments, the 3D guiding system is attached to the first object. Instead of being attached to the first objects, the guiding system may be an integral part of it.

When the relative arrangement of the first and second objects is influenced by other movements than the relative movement provided by e.g. a human operator, such a displaying of the information may be essential for obtaining the first preferred relative arrangement between the first and second objects. In the case of a dental or surgical treatment on a patient, the patient may move and this patient movement may be accounted for by real-time determining the relative position and/or real-time calculation of the information.

In some embodiments, the second object comprises a one or more units that are to be welded or glued together.

In some embodiments, the method comprises estimating a surface deformation of the second object when the second object e.g. is bend. In one case, a 3D model of a patient is obtained while the patent is sitting in one posture while during the movement of a scalpel towards an entry point on the patient's body, the patient is sitting in a different posture. This change of posture may cause problems. When the method comprises an estimation of the change of the patient's body during the change of posture, such problems may be avoided.

In some embodiments, the calculation of the information for guiding the first and second objects towards said first preferred relative arrangement takes into account the shape of the entry part of said first object.

In some embodiments, the first object comprises a drilling tool. The drilling tool may comprise a surgical or dental drilling tool configured for drilling into a body part, a tooth or the mandibular or maxillary bone of the patient.

In some embodiments, the first object comprises a dental drilling tool configured for drilling into a tooth or the mandibular or maxillary-bone of the patient.

In some embodiments, the method comprises deriving further preferred relative arrangements between the first and the second objects. The further preferred relative arrangements may comprise one or more additional preferred relative arrangements. The first preferred relative arrangement and the further additional preferred relative arrangements may together form a preferred path of the relative movement of the first and second objects. The method may comprise guiding said relative movement according to said preferred path. The 3D guiding system may be configured for guiding said relative movement according to said preferred path.

In some embodiments, the 3D guiding system comprises program code for deriving further preferred relative arrangements between the first and the second objects.

At least part of the further preferred relative arrangements may be such that they define intermediate relative arrangements of a path defined by the initial and the first preferred relative arrangement.

At least part of the further preferred relative arrangements may be such that they define an extension of a path defined by the initial and the first preferred relative arrangement, i.e. at least part of the further preferred relative arrangements represents a continuation of a relative movement of the first and second object in respect to the relative movement from the initial to the first preferred relative arrangement.

In some embodiments, one or more of said further preferred relative arrangements corresponds to an arrangement where at least a portion of the distal end of the first object is located below the surface of the second object. In the context of the present disclosure, the phrase "below the surface" may refer to a region located opposite to the first object relative to the surface of the second object when the objects are arranged in the initial relative arrangement.

In some embodiments, obtaining a 3D model of the second object comprises scanning at least a portion of the second object and/or scanning at least a portion of an impression of the second object, such that the 3D model comprises data relating to the surface of said second object. The scanned portion of the second object or of the impression of the second object may correspond to the region of the second object scanned using the 3D scanner during the movement procedure.

In some embodiments, the 3D model of the second object comprises data relating to the second object and data relating to a planned modification of the second object In some embodiments, the second object relates to the mandibular and/or maxillary of a patient and said planned modification corresponds to a dental implant or a hole which is planned to be defined in the mandibular or maxillary for accepting said dental implant. In some embodiments, the modification is planned based on information relating to the internal structure and/or the surface of the second object.

In some embodiments, the planned modification is taken into account when deriving the first preferred relative arrangement from said 3D model.

In some embodiments, the planned modification is taken into account by the program code for deriving the first preferred relative arrangement from said 3D model.

In some embodiments, the 3D model of the second object is obtained prior to the movement procedure.

In some embodiments, the second object comprises a part a patient body, such as a region of the patient body in which a surgical procedure is to be performed, such as a region comprising skin, muscular tissue, bone structure, and/or blood vessels.

In some embodiments, obtaining said 3D model comprises data from a scanning of the surface of the scanned region of said second object.

In some embodiments, scanning the surface of the scanned region of said second object provides a virtual 3D representation of the second object from which the 3D model may be obtained. The virtual 3D representation can e.g. be a point cloud from which the 3D model is generated by triangulation.

In some embodiments, a sub-surface scanning of the interior structure of the scanned region of said second object provides a virtual 3D representation of the interior structure of the second object from which the 3D model may be obtained. In some embodiments, the virtual 3D representation is at least in part obtained by a sub-surface scanning of the scanned region and/or target region of said second object, such as by Magnetic Resonance Imaging, by an X-ray scanning or by a CT scanning of the second object.

In some embodiments, the interior structure of the second object comprises nerves, root parts of teeth, or the mandibular and/or maxillary bone structure.

In some embodiments, the interior structure of the second object comprises nerves, bone structure, arteries, and veins of a patient's body.

In some embodiments, the 3D model of the second object is obtained by combining data obtained by scanning its surface and data obtained by scanning its interior structure, such that the 3D model comprises data relating to the surface and data relating to the interior structure of the second object.

In some embodiments, the 3D model of the second object comprises a 2D X-ray scan of the second object arranged relative to a 3D scanning of the surface of the second object, i.e. the 2D X-ray scan of the second object is arranged relative to a surface of the second object in the 3D model.

The target region may be part of the scanned region, such that the target region is scanned during the 3D scanning. The target region may be at least partly displaced from the scanned region, such that the 3D scanning provides a scan comprising one or more regions of the second object located outside the target region. The 3D scanning may comprise a scanning of off-target regions of the second object, where these off-target regions are linked to the target regions, such that determining the location of the off-target regions is used to determine the relative arrangement of the first and second object. This may be the case in applications where the form of the second object is well-defined and determined prior to applying the disclosure or where alignment marks are provided on a part of the second object which is displaced from the target region. The displaced scanned region is then scanned while the entry portion of the first object is arranged relative to the target region of the second object according to the first preferred relative arrangement.

In some embodiments, the 3D model is provided using a non-contact imaging method, such as a method based on electromagnetic or acoustic waves.

In some embodiments, the 3D guiding system is configured to provide a 3D scanning of the at least the scanned region of the second object.

In some embodiments, 3D scanning a region of the second object provides a mapping of the surface of the second object in the scanned region.

In some embodiments, 3D scanning a region of the second object provides a mapping of an interior part of the second object in the scanned region.

In some embodiments, each image or sub-scan is obtained in one shot, i.e. each sub-scan is acquired instantaneously without the use of e.g. a line-scanning technique. In a line-scanning technique a line of light is scanned across the scanning area and e.g. reflected light is collected over time as the line scans across the scanning area.

In some embodiments, the information is displayed by projecting a guiding signal onto the region of the second object.

In some embodiments, the information displaying device of the 3D guiding system comprises a projecting device configured for projecting a guiding signal onto a region of the second object, where the guiding signal is based on the information.

The guiding signal may be projected onto a point of contact, where contact is established between the first and second objects when arranged according to the first preferred relative arrangement.

The guiding signal may be guided towards a point of entry, where an entry part of said first object is to enter the target region of the second object.

The region of the second object onto which the guiding signal is projected may comprise the target region or at least part of said target region.

In some embodiments, the information displaying device of the 3D guiding system comprises a display and said information is displayed on said display as a guiding signal.

In some embodiments, the guiding signal comprises a positioning signal. The positioning signal may show the position of the target region on said second object i.e. the positioning signal may show where the distal end of the first object is to contact the second object.

The positioning signal may provide information relating to the relative position of the first object and the second object, such as to the position of the first object relative to a preferred path.

In some embodiments, the guiding signal comprises an orientation signal. The orientation signal may provide information relating to the relative orientation of the first object and the second object, such as to the relative orientation of the first and second objects compared to the relative orientation of a preferred path. The orientation signal may provide information relating to a difference in the orientation of the present relative arrangement compared to the orientation of the first preferred relative arrangement.

In some embodiments, the positioning signal comprises a relatively brighter spot and said orientation signal comprises a relatively less bright spot or vice versa.

In some embodiments, the positioning signal comprises a relatively smaller area spot and said orientation signal comprises a relatively larger area spot or vice versa.

In some embodiments, the positioning signal comprises a positioning color code, preferably configured such that the color of the position indicator changes when the first and second objects are approaching each other towards the first preferred relative arrangement.

In some embodiments, the orientation signal comprises an orientation color code, preferably configured such that the color of the orientation indicator changes when the first and second objects are approaching each other towards the first preferred relative arrangement.

In some embodiments, a cross sectional geometry of said positioning signal and/or of said orientation signal is selected from the group of a cross, a dot, a circle, or a polygon, such as a triangle, a square, rectangle, or a pentagon.

In some embodiments, the guiding signal comprises an indicator signal and the orientation signal coincides with said indicator signal when the first and second objects are arranged according to the orientation of the first preferred relative arrangement.

In some embodiments, the guiding signal comprises a distance indicator providing information relating to the distance between the first and second objects.

The orientation of the first object relative to a position in the target region of the second object may be expressed using a spherical coordinate system, where the spherical coordinate system is arranged such that its origin coincides with said position in the target region and the zenith direction coincides with the surface normal of the second object at said position. The position in the target region may be a point of entry wherein the entry part of the first object is to enter the second object. The preferred arrangement of the first object relative to the second object may then be expressed as a preferred azimuthal angle and a preferred inclination. The distance between the first and second objects may then be measured as the radial distance of the entry part from the position.

In some embodiments, the positioning signal and said orientation signal are arranged concentrically at least for some arrangements of the first and second objects. The orientation signal may be configured to surround the position signal at least when the present relative arrangement is close to the first preferred relative arrangement or to a further preferred relative arrangement.

In some embodiments, the 3D guiding system comprises means for controlling the position of the guiding signal based on the 3D scanning and the relative arrangement of the first and second objects.

In some embodiments, the position of the guiding signal is determined via the direction in which the guiding signal is emitted from a light source of the 3D guiding system. The means for controlling the position of the guiding signal may then comprise beam controlling optics and/or actuators for controlling the arrangement of the guiding signal light source relative to the other parts of the 3D guiding system.

In some embodiments, the 3D guiding system is configured for obtaining a pre-process plan describing a preferred path for the relative arrangement of the first and second objects during their relative movement towards the first preferred relative arrangement. In some embodiments, a pre-process plan is provided, said pre-process plan describing a preferred path for the relative arrangement of the first and second objects during their relative movement. The relative motion may be towards the first preferred relative arrangement. The relative motion may extend further than the first preferred relative arrangement along further preferred relative arrangements.

The preferred path may substantially be followed as the first and second objects approach the first preferred relative arrangement. Deviations form said preferred path may be corrected in real-time by either bringing the relative movement back to the planned preferred path or by real-time adapting the path.

The 3D scanning of the second object may provide a scanning of the surface of the second object in its scanning part. Techniques know for the skilled person may be used for this part of the procedure.

The concept of the disclosure is generic and may be applied in numerous applications such as for dental treatments, surgical treatments, drilling in structures such as walls wherein e.g. electrical wiring or water/gas pipes are present, or for welding or gluing different structures together.

The disclosure may also be applied for the alignment of larger structures such as for parking cars or for docking one structure in relation to another. The concept of the disclosure provides no limitations to the size of the object and the first object may e.g. be a shop docking a harbor or a space shuttle docking to a space station.

The disclosure may be applied in medical treatments such as for placing a stent in a blood vessel when e.g. performing a balloon angioplasty of the coronary artery or for intragastric balloon surgery.

In some embodiments, the 3D scanning provides a reading of the present relative arrangement of the objects. This may comprise the relative position and orientation of the first and second objects. The distance between the first and second objects may be determined from their relative position and/or by direct measurement.

Such a reading may be provided by comparing the result of the 3D scanning and the 3D model of the second object. In the case of a dental procedure, the 3D model may be of a set of teeth showing the surface and/or interior structure of the set of teeth. The 3D scanning may provide a virtual 3D representation of the surface of the set of teeth as seen from e.g. a drilling tool. By comparing the 3D model and the result of the 3D scanning, the present relative arrangement may be identified. Information for guiding the drill towards its first preferred relative arrangement may then be calculated and the information may be displayed to the dentist who then may provide a relative movement wherein the drill is moved towards the target region of the set of teeth. This movement procedure continues until the drill has reached the position and orientation according to the first preferred relative arrangement.

The disclosure may be applied in relation to a dental treatment for guiding a dentist when performing an operation on the dental situation of a patient. It may of significant importance that contact between the drill and the nerves in the teeth is avoided since a damaging of these nerves may have severe effects for the patient.

The first object may then be a dental tool, such as a dental drilling tool, onto which the 3D guiding system is attached. The second object may comprise part of the dental situation of the patient, such as a part of the teeth and/or of the mandibular or maxillary bone of the patient. The 3D model of the second object may be obtained from a virtual 3D representation of the dental situation by scanning the dental situation, such as by scanning the dental situation by means of an intraoral scanner and/or by scanning an impression of the dental situation.

The first preferred relative arrangement may then refer to an arrangement of the dental tool in relation to e.g. a tooth or the mandibular or maxillary bone of the patient.

A 3D model of the dental situation of the patient may be provided from a scanning of the teeth and/or the mandibular or maxillary bone. The surface of the teeth may be scanned by means of an optical based intraoral scanner or by scanning an impression of the dental situation. A CT-scan may provide knowledge of the location of the nerves in the dental situation and together with the scan of the surface of the set of teeth form the 3D model used for calculating the first preferred relative arrangement of the drill and the set of teeth. In fact the CT scanning may also provide information relating to the surface of the second object. The first preferred relative arrangement may be such that the drill contacts the surface of a tooth which is to be exposed to a procedure. The preferred orientation may be such that the drill can move along its longitudinal direction at least over some length without hitting a nerve. When the dentist moves the dental drilling tool with the attached 3D guiding system towards the dental situation, the 3D guiding systems displays the relative position of the drill and the dental situation. The displaying may comprise projecting a positioning signal onto the tooth in the target region where the drill touches the tooth, while the orientation signal may comprise a ring with a dot indicating the deviation of the azimuthal and inclination of the present orientation from the azimuthal and inclination of the orientation of the first preferred relative arrangement. When the dentist changes the orientation of the drilling tool, the ring and dot changes such that the dentist is guided towards the preferred arrangement of the drill relative to the dental situation of the patient.

When the disclosure is applied in relation to a dental implant treatment the first preferred relative arrangement of a dental drilling tool and e.g. the mandibular or maxillary bone of the patient such that the dental drilling tool is aligned to drill into the mandibular or maxillary bone. Prior to the commencement of the implant procedure, the vital structures such as the inferior alveolar nerve or the sinus are preferably identified. The shape and dimensions of the mandibular or maxillary bone may also be mapped such that the implant may be arranged in the most advantageous place and orientation. The 3D model of the dental situation of the set of teeth may be obtained from e.g. 2D radiographs, such as orthopantomographs or periapicals, or from a CT scan. The planning may involve the use of 3D CAD/CAM software In one work-flow for determining a first preferred relative arrangement, a CT scan of a patient's dental situation is obtained initially. From a 3D model of the dental situation formed from the CT scan, the position and orientation of an implant is planned. The position and orientation of the hole in the mandibular or maxillary which is to accept the dental implant is then planned from the planned implant position and orientation. From the planned hole/implant position and orientation, a modified 3D model of the second object is generated where the planned implant/implant hole is indicated. From the modified 3D model, the first preferred relative arrangement can be determined The disclosure may also be applied in relation the surgical procedures. In this case the first object may comprise a scalpel tool adapted to cut open the patient, where the 3D guiding system is attached to the scalpel tool. The second object may be the patient such that the 3D model comprises a model of the skin and preferably the parts of the body arranged below the skin of the patient. This may be blood vessels or bone structure. The first preferred relative arrangement may be such that a surgeon can cut open the patient in the target region without inflicting unnecessary damage to the patient once the guiding is followed by the surgeon. The position of the target region may be indicated with the position signal, which may comprise a cross or a dot. The orientation signal may be a larger ring surrounding the position signal. When cutting into the patient, i.e. bringing the scalpel further into the patient's body, the preferred orientation may change and further preferred arrangements may be calculated based on the 3D model. The orientation signal may change accordingly as the scalpel progresses guiding the surgeon to perform the preferred cut such that the extent of damage is mitigated.

Access to the part of the body may have been provided prior to the process, such as prior to the part of the method involving obtaining a 3D model of the second object. The 3D model may also be obtained initially and then a first procedure is performed to e.g. open the chest of the patient before the method according to the present disclosure is applied.

The requirement to the precision in the relative arrangement of the first and second objects may be very strict, such that the first preferred relative arrangement is unique. The precision requirement may be less strict, such that the first preferred relative arrangement may comprise an interval of relative arrangements. For example a gluing tool may have different azimuthal angles relative to an object onto which it is about to apply glue. When using a guiding signal comprising a positioning signal and/or an orientation signal the change of the signals which indicate that the first preferred relative arrangement has been reached may occur when the relative arrangement of the first and second objects is sufficiently close to the optimal relative arrangement such that it is within the required precision.

The 3D scanner of the 3D guiding system may comprise a number of parts, such as one or more probe light sources and one or more cameras configured to obtain a virtual 3D representation of said second object.

The 3D scanner may be constructed in various ways known to the skilled person.

One realization of a 3D scanner comprises a camera comprising an array of sensor elements and a probe light source configured for generating a probe light. The probe light may be transmitted towards the second object thereby illuminating at least the scanned region of the second object, and light returned from the second object may be transmitted to the array of sensor elements. The 3D scanner may further comprise a first optical system for imaging with a first depth of field on the camera at least part of the transmitted light returned from the second object to the array of sensor elements and a focus plane shifting device configured for varying the position of the focus plane on the second object. Further, the 3D scanner may be configures to obtain at least one image from said array of sensor elements and to determining the in-focus position(s) of each of a plurality of the sensor elements for a range of focus plane positions, or each of a plurality of groups of the sensor elements for a range of focus plane positions. The scanner may further be configured for transforming the in-focus data into 3D coordinates.

The camera may comprise a lens and a sensor array such as a CCD or CMOS chip. In some embodiments, a filter placed in front of the sensor array. The effect of the filter may be that only light with approximately the desired wavelength passes the filter. This makes it feasible to separate different light sources in the 3D scanner and remove most of the background light. Alternatively, the camera may be color sensitive.

The camera may be arranged such that it is configured to record images, from where the relative position and orientation of the first and second objects may be determined.

The 3D guiding system may comprise one or more light sources such as a probe light source for the 3D scanner and a signal light source for providing a guiding signal. The light sources may be lasers, variable output-powered laser, light emitting diodes (LED), halogen spots or other spotlights. The generated light may be supplied directly from a light source arranged e.g. near a distal end of the first object, or it may be supplied with optical waveguides, such as optical fibers. In some applications it might be relevant to use monochromatic, coherent or polarized light. Note that the light may be projected onto the surface of the second object without damaging the surface even when lasers provide the light. The probe light source and/or the signal light source may emit light in the ultraviolet range, in the visible range and/or in the infrared range. The probe light source and/or the signal light source may be adapted to emit coherent light, polarized light, monochromatic light, or light at different frequencies, such as light in two or more frequency ranges. Various filters may be applied to the probe light source and/or to the signal light source.

The 3D guiding system may work with only one light source, but for many purposes it is advantageous to have several such as at least two light sources. One or more probe light sources may be used in the 3D scanner while one or more signal light sources may be configured to provide the guiding signal projected onto the second object.

For some applications, the light sources are preferably as small as possible to minimize the dimensions of the 3D guiding system. It is contemplated that the light source may have a cross section perpendicular to the direction of emitted light of less than 5 mm$^2$, preferably less than 4 mm$^2$, for example less than 3 mm$^2$, such as less than 2 mm$^2$, for example less than 1 mm$^2$, such as less than 0.5 mm$^2$, for example less than 0.25 mm$^2$.

Handheld embodiments of the invention may comprise motion sensors such as accelerometers and/or gyros. These micro electro mechanical systems (MEMS) may measure all motion in 3D, i.e., both translations and rotations for the three principal coordinate axes.

Disclosed is also a computer program product comprising program code means for causing a data processing system to perform the method according to the present disclosure when said program code means are executed on the data processing system, and a computer program product comprising a computer-readable medium having stored there on the program code means.

In some embodiments, a touch sensor is arranged in connection with the distal end of the first object, such that the touch sensor is adapted to register contact with the second object. The touch sensor may comprise a tactile component at the distal end. The touch sensor may be a capacitive sensor.

Disclosed is also a nontransitory computer readable medium storing thereon a computer program, where said computer program is configured for causing computer-assisted implementation of one or more parts of the method according to the present disclosure.

Disclosed is a system for guiding a relative movement of a first object and a second object, said system comprising:
  a 3D guiding system configured for being attached onto the first object, where said 3D guiding system comprises a 3D scanner;
  a non-transitory computer-readable medium configured for at least temporary storing
    i. a 3D model of the second object;
    ii. program code for deriving from said 3D model a first preferred relative arrangement between the first and second objects;
    iii. program code for determining a present relative arrangement of the first and second objects from a result of a 3D scanning of the second object; and
    iv. program code for calculating information for guiding the relative movement of the first and second objects towards said first preferred relative arrangement from said present relative arrangement.

EMBODIMENTS

1. A method for providing a guided relative movement of a first object and a second object, said method comprising:
  obtaining the first object onto which a 3D guiding system is attached, where said 3D guiding system comprises a 3D scanner;
  obtaining the second object and a 3D model of the second object, and deriving from said 3D model a first preferred relative arrangement between the first and second objects;
  performing a movement procedure comprising:
    a) 3D scanning at least a region of said second object using said 3D scanner and determining a present relative arrangement of the first and second objects from a result of the 3D scanning;
    b) calculating information for guiding the relative movement of the first and second objects towards said first preferred relative arrangement from said present relative arrangement; and
    c) providing a relative movement of said first and second objects towards the first preferred relative arrangement, where the calculated information is used for guiding the relative movement.

2. The method according to embodiment 1, wherein one or more of a), b) and c) are performed in real-time.

3. The method according to any of the previous embodiments, wherein the movement procedure comprises repeating one or more of a), b) and c) a number of times.

4. The method according to any of the previous embodiments, wherein the relative movement of the first and second objects is substantially continuous and a) and/or b) are performed during the relative movement.

5. The method according to any of the previous embodiments, wherein the information is displayed using an information displaying device of said 3D guiding system.

6. The method according to any of the previous embodiments, wherein the method comprises arranging said first and second objects in an initial relative arrangement and where said information is used for guiding the first and second objects from the initial relative arrangement to the first preferred relative arrangement.

7. The method according to any of the previous embodiments, wherein the 3D guiding system comprises a motion sensor adapted to perform a motion measurement of the movement of the first object, and where the present relative arrangement of the first and second objects is determined from said motion measurement.

8. The method according to any of the previous embodiments, wherein the 3D guiding system comprises an orientation sensor adapted to perform an orientation measurement of the first object, and where the present relative arrangement of the first and second objects is determined from said orientation measurement.

9. The method according to any of the previous embodiments, wherein said 3D scanning is performed in real-time.

10. The method according to any of the previous embodiments, wherein said information is calculated in real-time.

11. The method according to any of the previous embodiments, wherein said information is displayed in real-time.

12. The method according to any of the previous embodiments, wherein said first object contacts said second object in a target region of the second object when the first and second objects are arranged in said first preferred relative arrangement.

13. The method according to any of the previous embodiments, wherein said first object comprises a distal end which is configured to contact the target region of the second object.

14. The method according to any of the previous embodiments, wherein said distal end comprises an entry part configured to enter the target region of said second object.

15. The method according to any of the previous embodiments, wherein deriving the first preferred relative arrangement takes into account the shape of the entry part of said first object.

16. The method according to any of the previous embodiments, wherein the calculation of the information for guiding the first and second objects towards said first preferred relative arrangement takes into account the shape of the first object.

17. The method according to any of the previous embodiments, wherein the first object comprises a dental drilling tool configured for drilling into a tooth or the mandibular or maxillary-bone of the patient.

18. The method according to any of the previous embodiments, wherein the first object comprises a scalpel.

19. The method according to any of the previous embodiments, wherein the method comprises deriving further preferred relative arrangements between the first and the second objects.

20. The method according to embodiment 19, wherein the first preferred relative arrangement and the further additional preferred relative arrangements together forms a preferred path of the relative movement of the first and second objects, and said method comprises guiding said relative movement according to said preferred path.

21. The method according to any of the previous embodiments, wherein one or more of said further preferred relative arrangements corresponds to an arrangement where at least a portion of the distal end of the first object is located below the surface of the second object.

22. The method according to any of the previous embodiments, wherein obtaining a 3D model of the second object comprises scanning at least a portion of the second object and/or scanning at least a portion of an impression of the second object.

23. The method according to any of the preceding embodiments wherein the 3D model of the second object comprises data relating to the second object and data relating to a planned modification of the second object 24. The method according to any of the preceding embodiments wherein the second object relates to the mandibular and/or maxillary of a patient and said planned modification corresponds to a dental implant or a hole which is planned to be defined in the mandibular or maxillary for accepting said dental implant.

25. The method according to any of the preceding embodiments wherein the modification is planned based on information relating to the internal structure and/or the surface of the second object.

26. The method according to any of the preceding embodiments wherein the planned modification is taken into account when deriving the first preferred relative arrangement from said 3D model.

27. The method according to any of the preceding embodiments wherein the 3D model of the second object is obtained prior to the movement procedure.

28. The method according to any of the previous embodiments, where the second object comprises a part a patient body, such as a region of the patient body in which a surgical procedure is to be performed, such as a region comprising skin, muscular tissue, bone structure, and/or blood vessels.

29. The method according to any of the preceding embodiments, wherein said second object is a dental situation of a patient, such as a dental situation comprising a tooth, a part of a tooth and/or at least part of the mandibular or maxillary bone of the patient, and where the 3D model of the second object is obtained by scanning the dental situation, such as by scanning the dental situation by means of an intraoral scanner or scanning an impression of the dental situation.

30. The method according to any of the previous embodiments, wherein obtaining said 3D model comprises a scanning of the surface of the scanned region of said second object.

31. The method according to any of the previous embodiments, wherein obtaining said 3D model comprises a sub-surface scanning of the scanned region and/or target region of said second object, such as by Magnetic Resonance Imaging, by an X-ray scanning or by a CT scanning of the second object, such that the 3D model comprises an interior structure of the second object.

32. The method according to any of the previous embodiments, wherein the 3D model comprises a 2D X-ray scan of the second object arranged relative to a 3D scanning of the surface of the second object.

33. The method according to any of the previous embodiments, wherein the interior structure of the second object comprises nerves, root parts of teeth, or the mandibular and/or maxillary bone structure.

34. The method according to any of the previous embodiments, wherein the interior structure of the second object comprises nerves, bone structure, arteries, and veins of a patient's body.

35. The method according to any of the previous embodiments, wherein the 3D model of the second object is obtained by combining data obtained by scanning its surface and data obtained by scanning its interior structure, such that the 3D model comprises data relating to the surface and data relating to the interior structure of the second object.

36. The method according to any of the previous embodiments, wherein 3D scanning a region of the second object provides a mapping of the surface of the second object in the scanned region 37. The method according to any of the previous embodiments, wherein 3D scanning a region of the second object provides a mapping of an interior part of the second object in the scanned region.

38. The method according to any of the previous embodiments, wherein said information is displayed by projecting a guiding signal onto a region of the second object.

39. The method according to any of the previous embodiments, wherein the region of the second object onto which the guiding signal is projected comprises the target region or at least part of said target region.

40. The method according to any of the previous embodiments, wherein said information displaying device of the 3D guiding system comprises a display and said information is displayed on said display as a guiding signal.

41. The method according to any of the previous embodiments, wherein said guiding signal comprises a positioning signal.

42. The method according to embodiment 41, wherein said positioning signal shows the position of the target region on said second object.

43. The method according to embodiment 41 or 42, wherein said positioning signal provides information relating to the relative position of the first object and the second object.

44. The method according to any of the previous embodiments, wherein said guiding signal comprises an orientation signal.

45. The method according to embodiment 44, wherein said orientation signal provides information relating to the relative orientation of the first object and the second object.

46. The method according to embodiment 44 or 45, wherein said orientation signal provides information relating to a difference in the orientation of the present relative arrangement compared to the orientation of the first preferred relative arrangement.

47. The method according to any of the previous embodiments, wherein said positioning signal comprises a relatively brighter spot and said orientation signal comprises a relatively less bright spot.

48. The method according to any of the previous embodiments, wherein said positioning signal comprises a relatively smaller area spot and said orientation signal comprises a relatively larger area spot.

49. The method according to any of the previous embodiments, wherein said positioning signal comprises a positioning color code configured such that the color of the position indicator changes when the first and second objects are approaching the first preferred relative arrangement.

50. The method according to any of the previous embodiments, wherein said orientation signal comprises an orientation color code configured such that the color of the orientation indicator changes when the first and second objects are approaching the first preferred relative arrangement.

51. The method according to any of the previous embodiments, wherein a cross sectional geometry of said positioning signal and/or of said orientation signal is selected from the group of a cross, a dot, a circle, or a polygon, such as a triangle, a square, rectangle, or a pentagon.

52. The method according to any of the previous embodiments, wherein the guiding signal comprises an indicator signal, and wherein the orientation signal coincides with said indicator signal when the first and second objects are arranged according to the orientation of the first preferred relative arrangement.

53. The method according to any of the previous embodiments, wherein the guiding signal comprises a distance indicator providing information relating to the distance between the first and second objects.

54. The method according to any of the previous embodiments, wherein said positioning signal and said orientation signal are arranged concentrically at least for some arrangements of the first and second objects.

55. The method according to any of the previous embodiments, wherein a pre-process plan is provided, said pre-process plan describing a preferred path for the relative arrangement of the first and second objects during their relative movement towards the first preferred relative arrangement.

56. The method according to any of the previous embodiments, wherein the preferred path substantially is followed as the first and second objects approach the first preferred relative arrangement.

57. The method according to any of the previous embodiments, wherein deviations form said preferred path are corrected real-time by either bringing the relative movement back to the planned preferred path or by real-time adapting the path.

BRIEF DESCRIPTION OF THE DRAWINGS

The above and/or additional objects, features and advantages of the present disclosure, will be further elucidated by the following illustrative and non-limiting detailed description of embodiments of the present disclosure, with reference to the appended drawings, wherein.

In the following description, reference is made to the accompanying figures, which show by way of illustration how the disclosure may be practiced.

Figure 1:
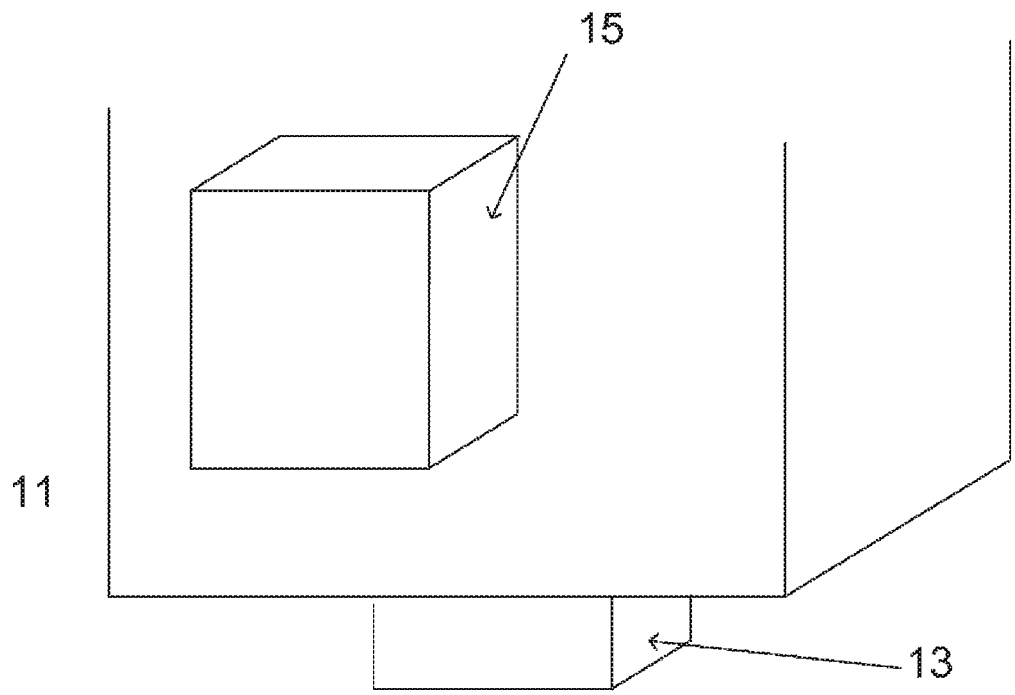
FIG. 1 shows a schematic presentation of a first object and a second object where a 3D guiding system is attached to the first object.
Figure 1:
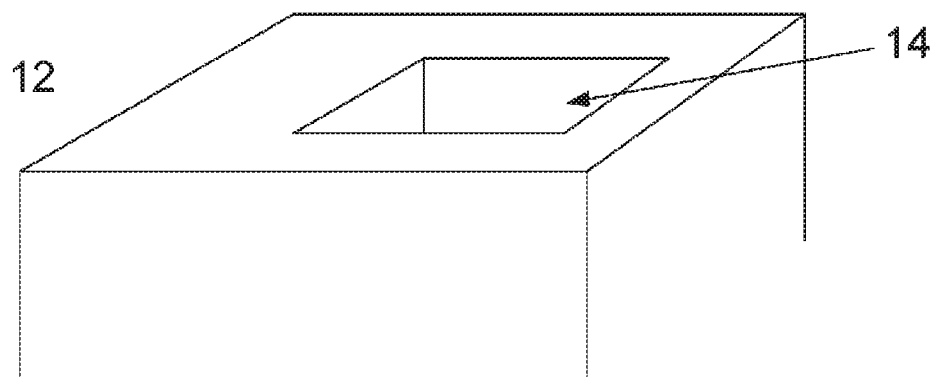

FIG. 1 shows a schematic presentation of a first object and a second object with a 3D guiding system attached to the first object.

The first object 11 has at its distal end a structure 13 which is configured to mate with a recess 14 at the target region of the second object 12. In this example the first preferred relative arrangement is such that the structure 13 is mated with the recess 14. The 3D guiding system 15 is attached to the first object 11, such that it can provide 3D scanning of the surface of the second object as the first and second objects approach the first preferred relative arrangement.

The relative movement of the first object 11 and the second object 12 may be provided by an operator or by e.g. a robotic device not illustrated in the figure. During the relative motion the guiding system 15 provides a real-time 3D scanning of the second object and the result of the 3D scanning is used for calculating information that is provided to e.g. an operator in real-time in the form of a guiding signal projected onto the second object.

In this example, the recess is visible such that the first preferred relative arrangement easily can be identified by an operator. In many applications, the first preferred relative arrangement is not visually accessible, but depends in an inner structure of the second object. The can e.g. be the case in a dental procedure, where the roots of a patient's tooth influences the first preferred relative arrangement, or in a surgical procedure where the position of bone structure and arteries below the patient's skin can be of importance.

FIG. 2 shows a schematic presentation of a dental application of the disclosure.

Figure 2A:
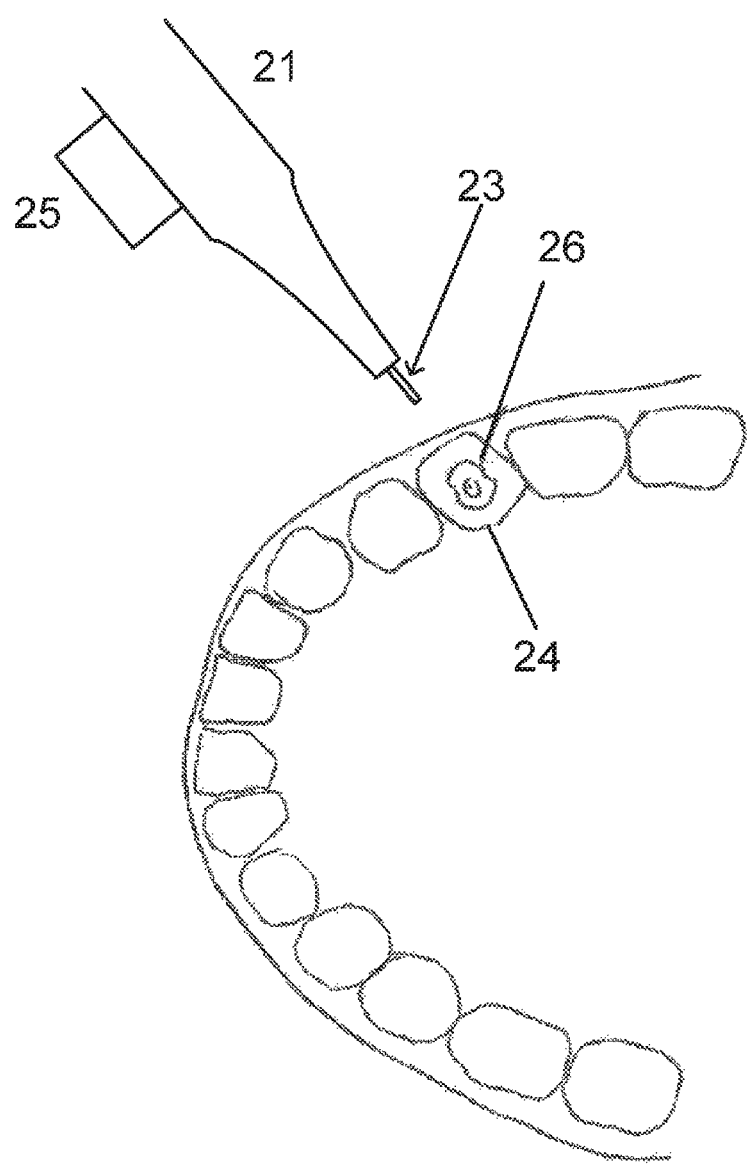
FIGS. 2a and 2b show a schematic presentation of a dental application of the disclosure.

In FIG. 2a, the first object is a dental drilling tool 21 while the second object is part of the dental situation of a patient. In this example, the method and the 3D guiding system is described in relation to a procedure for preparing the patient's mandibular or maxillary bone for accepting a dental implant, but the disclosure is generic and is not limited to this dental application. The drilling procedure is for providing a hole in the mandibular or the maxillary bone such that the implant may be arranged as a root-form endosseous implant.

The 3D model can be formed by combining surface data from a surface scanning and data relating to the interior structure obtained by X-ray based scanning showing the interior structure of at least part of the set of teeth and the mandibular or maxillary bone. Preferably the scanning showing the interior structure provides information relating to the location of the nerves in the set of teeth, such as the inferior Alveolar nerve and/or the mental nerve, such that the guiding system can guide the motion of the drilling tool in a manner whereby drilling into these nerves is prevented. The sub-surface scanning determining the interior structure of the tooth may comprise a CT scanning of the dental situation. The tooth originally being located at the site where the implant is to be arranged may have been removed prior to the drilling. The first preferred relative arrangement may thus be such that the drilling tool when starting to drill will provide the hole for the implant without colliding with the nerves.

The 3D guiding system 25 is attached to the dental drilling tool 21. The 3D scanner of the 3D guiding system may be configured for intraoral scanning of the teeth to provide a virtual 3D representation of the set of teeth, from which virtual 3D representation a new 3D model of the dental situation may be determined on the fly. From a comparison of the new 3D model and the obtained 3D model, the present relative arrangement may be determined.

A guiding signal 26 is projected on the target region of a tooth 24 by the 3D guiding system. The guiding signal illustrated here is a slightly deformed circular structure due to the shape of the tooth. The guiding signal 26 comprises a position signal and an orientation signal here illustrated as a dot in the center and the outer ring, respectively. The inner one of the two rings is an indicator signal ring showing the inclination of the first preferred relative arrangement. The 3D guiding system 25 is configured for directing the guiding signal onto the target region where the dental drilling tool 21 must drill into the tooth. The guiding signal 26 may be directed using e.g. mirrors or optical waveguides, such as optical waveguides.

The guiding signal can also be visualized by an information displaying device on which the information is visualized using e.g. a screen. The screen can be an integral part of the 3D guiding system.

Figure 2B:
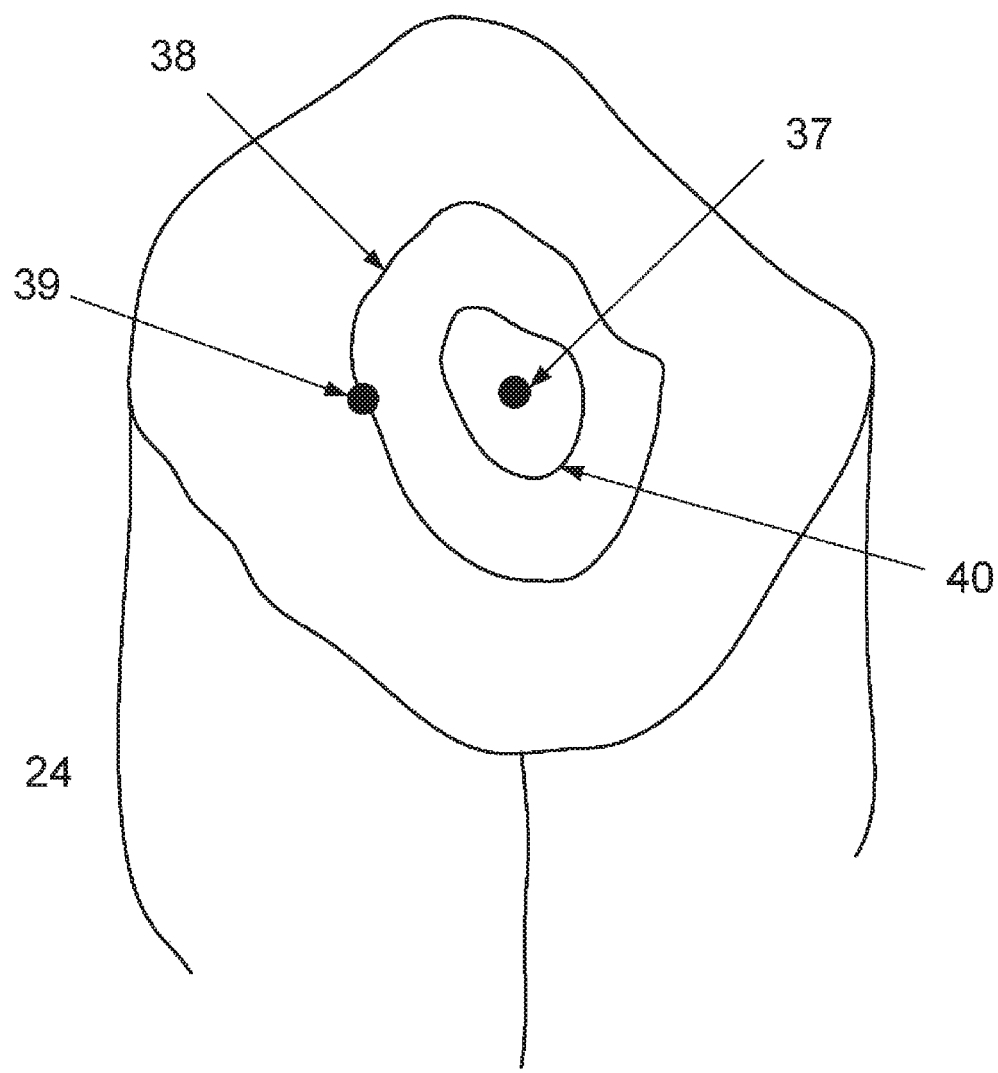

FIG. 2b shows a close-up of the tooth 24 and guiding signal of FIG. 2a, where the guiding signal consist of the position signal 37, an indicator signal ring 40, and an orientation signal with an orientation signal ring 38 and an orientation signal dot 39. The orientation signal dot 39 and the indicator signal ring 40 show the azimuthal angle and the inclination of the first preferred relative arrangement, respectively.

FIG. 3 illustrates a guiding signal according to the disclosure and the change of the guiding signal during a relative movement of the first and second objects.

The first object 31 may e.g. be a scalpel configured for cutting into the second object, i.e. into the patient. The FIGS. 3a-3c illustrate the change of the guiding signal 36 as the scalpel approaches the skin of the patient to a first preferred relative arrangement where the distal end of the scalpel is in contact with the target region of the patient skin.

Figure 3A:
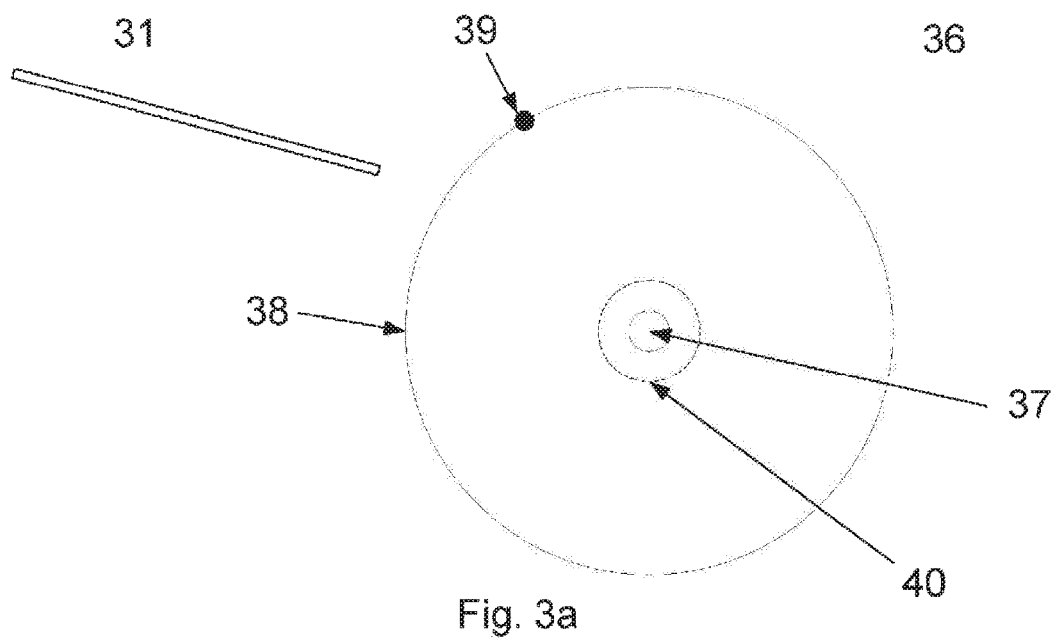
FIGS. 3a, 3b and 3c illustrate a guiding signal according to the disclosure and the change of the guiding signal during a relative movement of the first and second objects.

In FIG. 3a the scalpel is not in contact with the patient skin. The 3D guiding system 3D scans the surface of the patient, calculates the information, and projects the guiding signal 36 onto the patient skin thereby guiding the surgeon to the target region of the skin. The guiding signal 36 comprises a position signal 37 and an orientation signal 38, 39. Here the orientation signal comprises an orientation signal ring 38 (full line circle) and an orientation signal dot 39. The orientation signal ring 38 provides a measure of the inclination of the scalpel in the present relative arrangement. The indicator signal ring 40 (dotted line circle) of the indicator signal shows the inclination of the first preferred relative arrangement. The orientation signal dot 39 shows the azimuthal angle of the first preferred relative arrangement.

Figures 3B, 3C:
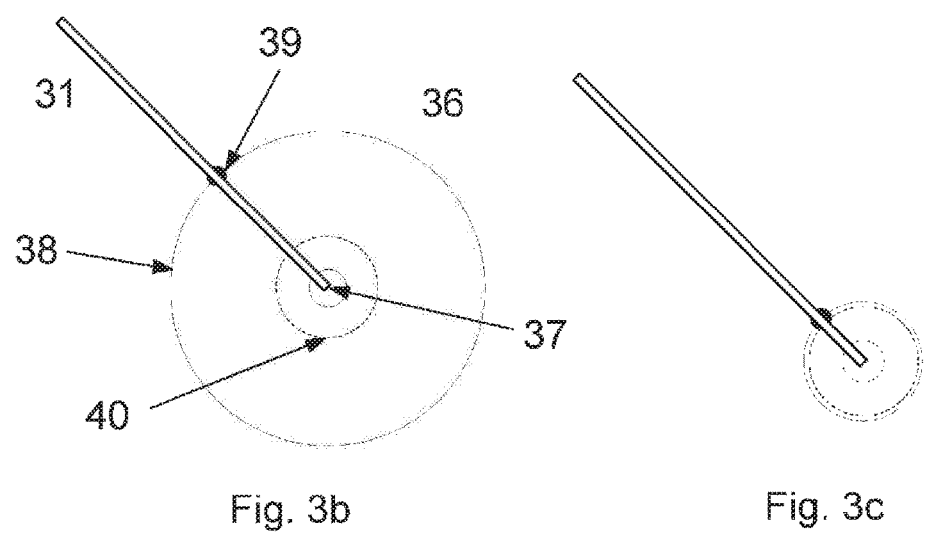

In FIG. 3b the scalpel has been placed such that its distal end contacts the patient skin at the target region and such that the azimuthal angle of the present relative arrangement matches that of the first preferred relative arrangement. Compared with the present relative arrangement of FIG. 3a the inclination is also closer to the first preferred relative arrangement as seen by the decrease in the radius of the orientation signal ring 38 towards the indicator signal ring 40.

In FIG. 3c the inclination of the scalpel is optimized such that the orientation signal ring (full line) coincides with the indicator signal ring (dotted line). The scalpel is now arranged according to the first preferred relative arrangement and the surgeon is ready to perform a cut into the patient's skin.

Figure 4A:
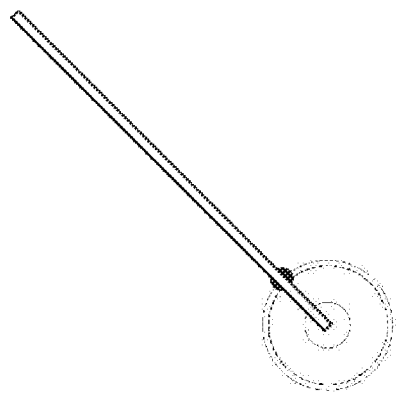
FIGS. 4a and 4b illustrate a guiding signal according to the disclosure and the change of the guiding signal during a relative movement of the first and second objects.

FIG. 4 illustrates a guiding signal according to the disclosure and the change of the guiding signal during a relative movement of the first and second objects.

Figure 4B:
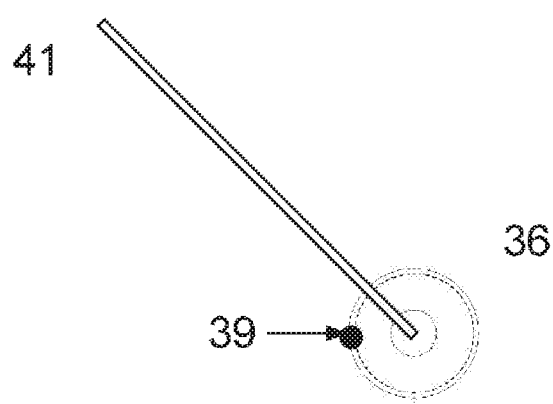

In FIG. 4, the preferred relative arrangement of the scalpel and the patients skin/body changes as the surgeon cuts into the patient and a further preferred relative arrangement is illustrated in FIG. 4b. Here the azimuthal angle of the further preferred relative arrangement differs from that of the first preferred relative arrangement as indicated by the movement of the orientation signal dot 39 and the surgeon needs to adjust the azimuthal angle of the scalpel relative to the body. In real-life, the change between preferred relative arrangements may often be smooth and gradual.

The steps illustrated in FIGS. 3 and 4 are generic for the disclosure and a similar relative movement could be seen for a dental treatment or a welding of two metal plates.

Figure 5:
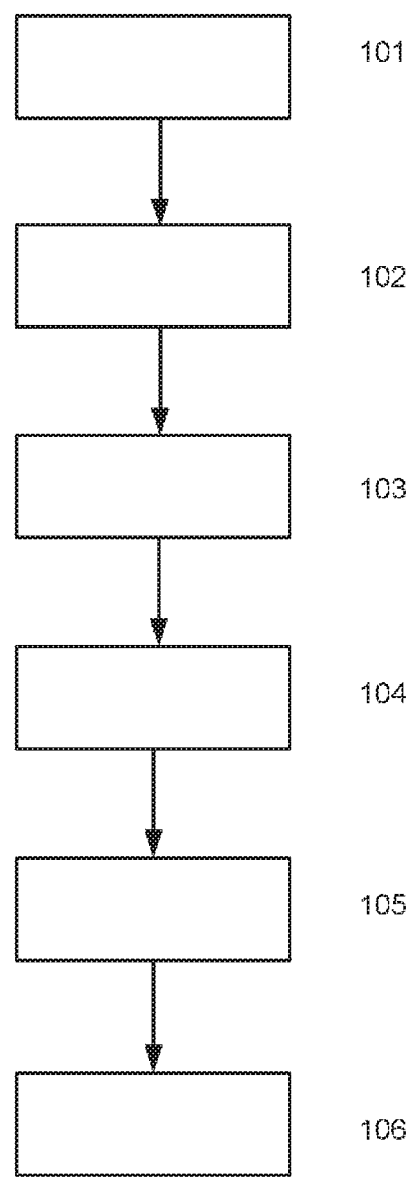
FIG. 5 shows a schematic of a method according to the present disclosure

FIG. 5 shows a schematic of a method according to the present disclosure Initially in step 101 the first object is obtained. On the first object, a 3D guiding system is attached, where said 3D guiding system comprises a 3D scanner.

In step 102 the second object and a 3D model of the second object is obtained. The second object and the 3D model of this may have an interior structure which is to be kept clear of during a modification of the second object.

In step 103, a first preferred relative arrangement between the first and second objects is derived from said 3D model. The first preferred relative arrangement may such that the first object keeps clear of the interior structure during a modification of the second object by the first object.

The movement procedure comprises steps 104-106:

In step 104 a 3D scanning at least a region of said second object using said 3D scanner is performed and a present relative arrangement of the first and second objects is determined from a result of the 3D scanning.

In step 105 the information for guiding the relative movement of the first and second objects towards said first preferred relative arrangement from said present relative arrangement is calculated.

In step 106 a relative movement of said first and second objects towards the first preferred relative arrangement is provided, where the calculated information is used for guiding the relative movement.

Figure 6:
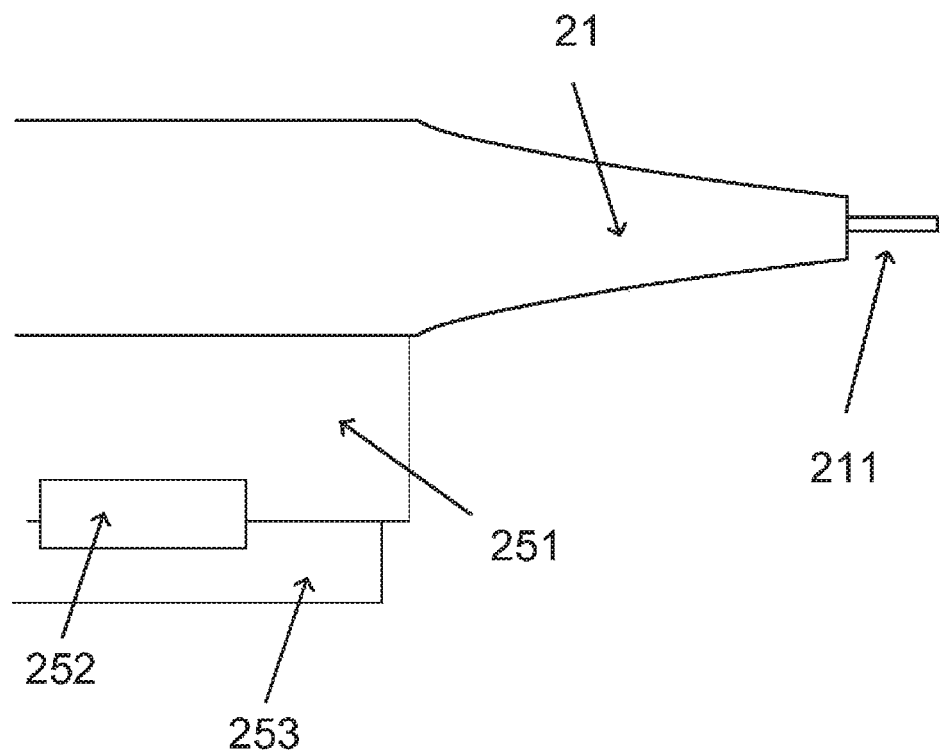
FIG. 6 shows a schematic of a first object with a 3D guiding system according to the present disclosure.

FIG. 6 shows a schematic of a first object with a 3D guiding system according to the present disclosure.

The 3D guiding system is attached to a dental drilling tool 21 with a distal end 211. The 3D guiding system comprises a 3D scanner 251 configured for performing a 3D scanning of the second object when this is arranged within the view of the 3D scanner 251. The 3D guiding system further comprises a non-transitory computer-readable medium 252. This medium stores a 3D model of the second object and various program code for e.g. determining a present relative arrangement of the first and second objects from a result of a 3D scanning of the second object, and for calculating information for guiding the relative movement of the first and second objects towards a first preferred relative arrangement from said present relative arrangement. Based on the calculated information, the information displaying device 253 (here a laser system configured for providing the guiding signal) projects the guiding signal onto the target region of the second object (here a dental situation). The dental situation can be a tooth from which the drill is intended to remove tooth material, or a maxillary or mandibular bone into which the drill is intended to form a hole for an implant.

Figure 7:
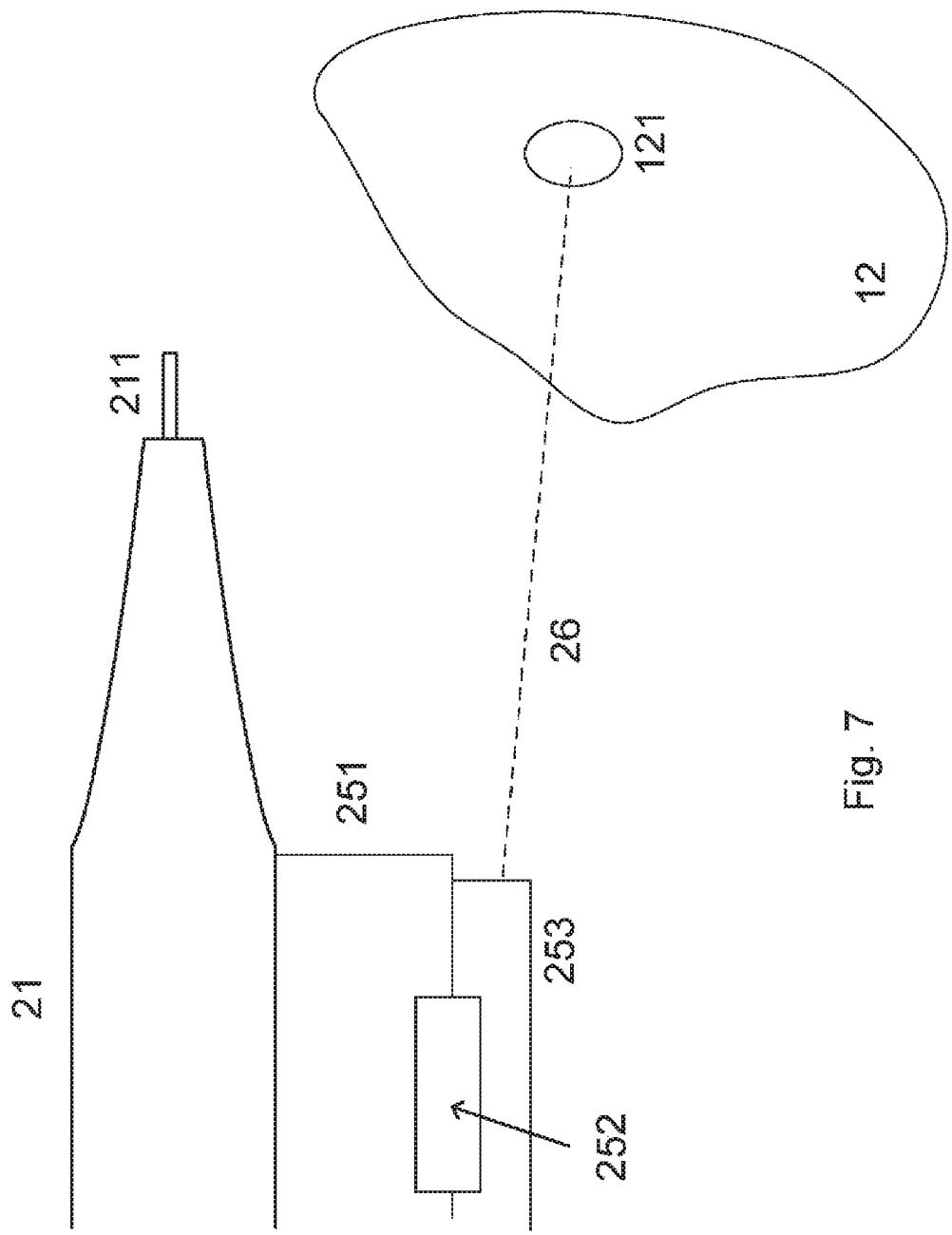
FIGS. 7 and 8 show a schematic of how an embodiment of the 3D guiding system guides the first object towards a first preferred relative arrangement.
Figure 8:
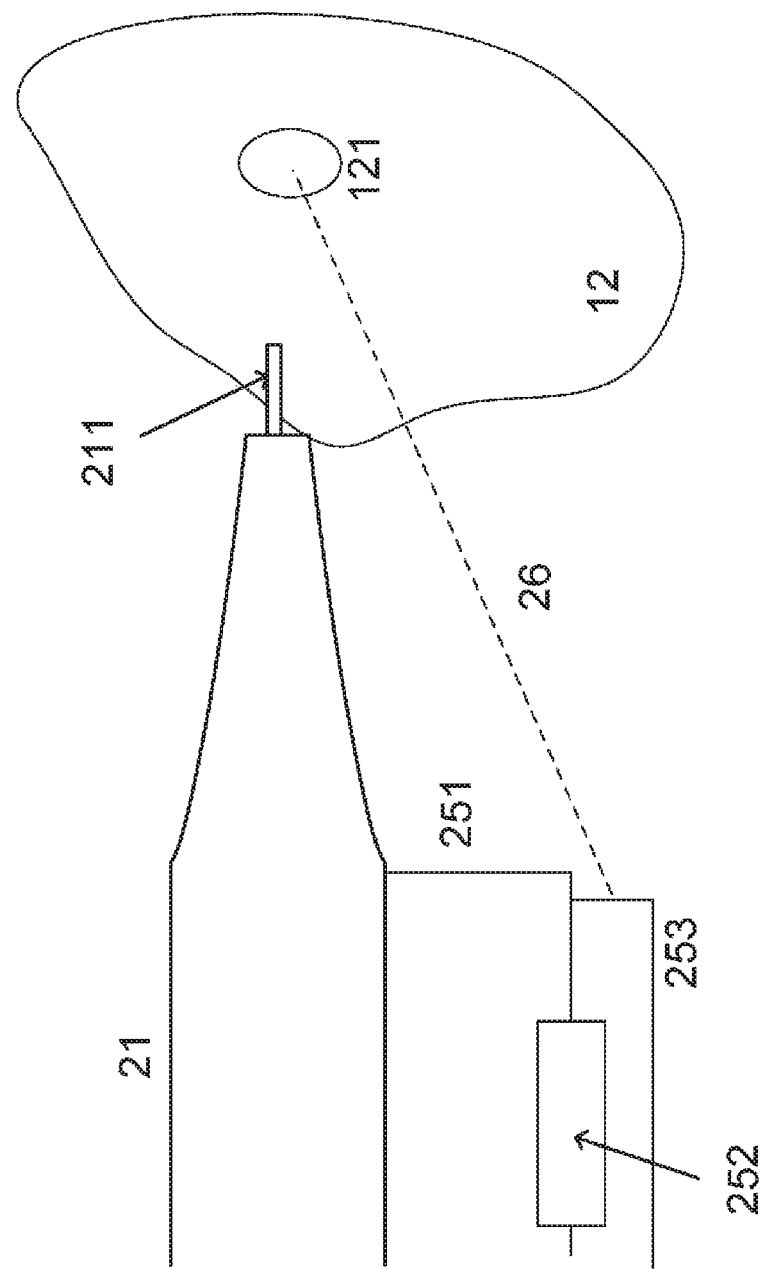

FIGS. 7 and 8 shows a schematic of how an embodiment of the 3D guiding system guides the first object towards a first preferred relative arrangement. The 3D guiding system is attached onto the first object 21 (here illustrated as a dental drilling tool) and comprises a 3D scanner 251 configured for performing a 3D scanning of a region of the second object 12. The 3D guiding system further comprises a non-transitory computer-readable medium 252 and an information displaying device 253, which here is a laser system configured for projecting the guiding signal 26 onto the target region 121 of the second object 12. Program code stored on the non-transitory computer-readable medium 252 calculates information relating to where the guiding signal 26 is to be projected on the second object 12, and actuators and/or optical components in the information displaying device 253 are controlled based on this information such that the guiding signal is projected onto the correct part of the second object. The shape of the guiding signal and the direction in which it is emitted is adjusted as the relative position of the first and second objects changes. FIG. 8 illustrates the situation where the first object is brought closer to the second object than in FIG. 7, and where the first object has been moved slightly along the surface of the second object. The direction of the guiding signal is accordingly adjusted such that the guiding signal still is projected onto the target region. Further the shape is adjusted if the relative orientation changes.

Some embodiments have been described and shown in detail, the disclosure is not restricted to them, but may also be embodied in other ways within the scope of the subject matter defined in the following claims. In particular, it is to be understood that other embodiments may be utilised and structural and functional modifications may be made without departing from the scope of the present disclosure.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

What is claimed is:

1. A 3D guiding system for guiding the movement of a dental tool towards a preferred arrangement relative to a dental situation of a patient, wherein the dental situation comprises a tooth, a part of a tooth and/or at least part of the mandibular or maxillary bone of the patient, where the 3D guiding system comprises:
   a 3D scanner configured for performing a 3D scanning of the patient's set of teeth, where the 3D scanner is attached to said dental tool; and
   a non-transitory computer-readable medium configured for at least temporarily storing:
      a 3D model of the patient's set of teeth;
      program code for determining a present relative arrangement of the dental tool and the dental situation from a result of a 3D scanning of the teeth and program code for calculating information for guiding the relative movement of the dental tool towards a first preferred relative arrangement at the teeth from said present relative arrangement; and
      an information displaying device configured for displaying the calculated information to an operator.

2. The 3D guiding system according to claim 1, wherein said 3D model comprises data relating to an interior structure of the teeth and/or the nerves or root parts of the teeth.

3. The 3D guiding system according to claim 1, wherein said 3D model comprises data relating to the mandibular or maxillary bone of the patient.

4. The 3D guiding system according to claim 1, where the dental tool comprises a drill.

5. The 3D guiding system according to claim 4, where in the first preferred relative arrangement at least a portion of the drill is located below the surface of a tooth or the mandibular or maxillary bone of the patient.

6. The 3D guiding system according claim 1, wherein the 3D guiding system comprises program code for deriving further preferred relative arrangements between the dental tool and the patient's set of teeth, and wherein the first preferred relative arrangement and the further preferred relative arrangements together form a preferred path of the relative movement of the dental tool towards the set of teeth, and said 3D guiding system is configured for guiding said relative movement according to said preferred path.

7. The 3D guiding system according to claim 1, wherein the 3D model comprises data relating to a planned modification of the second object.

8. The 3D guiding system according to claim 7, wherein the planned modification corresponds to a hole in the mandibular or maxillary jaw bone for accepting a dental implant.

9. The 3D guiding system according to claim 8, and where said preferred path is configured to provide that the dental tool when guided along the preferred path will drill said hole into the mandibular or maxillary jaw bone.

10. The 3D guiding system according to claim 8, wherein the program code for deriving the first preferred relative arrangement from said 3D model is configured to take the planned modification into account.

11. The 3D guiding system according to claim 1, wherein said 3D model comprises data relating to a surface of a scanned region of said patient's set of teeth.

12. The 3D guiding system according to claim 8, wherein the modification is planned based on information relating to the internal structure and/or the surface of the patient's set of teeth.

13. The 3D guiding system according to claim 1, wherein determining the present relative arrangement comprises determining the rotation and translation required to provide a correct alignment between the obtained 3D model and the result of the 3D scanning.

14. The 3D guiding system according to claim 1, wherein the result of the 3D scanning is used to generate a new 3D model of the second object as seen in the view of the present relative arrangement, and where determining the present relative arrangement of the first and second objects comprises comparing the new 3D model and the obtained 3D model.

15. The 3D guiding system according to claim 14, wherein comparing the new 3D model and the obtained 3D model comprises rotating and translating the obtained 3D model and/or the new 3D model such that they are aligned correctly and determining the present relative arrangement based on the extent of rotation and translation required to provide the correct alignment.

16. The 3D guiding system according to claim 1, wherein the method comprises determining a guiding signal based on the calculated information and displaying the guiding signal using an information displaying device of said 3D guiding system.

17. The 3D guiding system according to claim 16, wherein the information displaying device projects the guiding signal onto the second object.

18. The 3D guiding system according to claim 16, wherein the information displaying device comprises a display and the guiding signal is visualized in said display.

19. A method for a 3D guiding system for guiding the movement of a dental tool towards a preferred arrangement relative to a dental situation of a patient, wherein the dental situation comprises a tooth, a part of a tooth and/or at least part of the mandibular or maxillary bone of the patient, where the method comprises:
  performing a 3D scanning of the patient's set of teeth with a 3D scanner, where the 3D scanner is attached to said dental tool; and
  temporarily storing:
    a 3D model of the patient's set of teeth;
    program code for determining a present relative arrangement of the dental tool and the dental situation from a result of a 3D scanning of the teeth and program code for calculating information for guiding the relative movement of the dental tool towards a first preferred relative arrangement at the teeth from said present relative arrangement; and
    an information displaying device configured for displaying the calculated information to an operator.

* * * * *